US008956855B2

(12) United States Patent
Cognard et al.

(10) Patent No.: US 8,956,855 B2
(45) Date of Patent: Feb. 17, 2015

(54) PORTABLE CRYOGENIC CONTAINER (75) Inventors: Eric Cognard, Fontenai les Louvets (FR); Juan Moreno, College Station, TX (US)

(73) Assignee: ST Reproductive Technologies, LLC, Navasota, TX (US)

(*) Notice: Subject to any disclaimer, the term of this patent is extended or adjusted under 35 U.S.C. 154(b) by 266 days.

(21) Appl. No.: 13/478,791

(22) Filed: May 23, 2012

(65) Prior Publication Data
US 2012/0297797 A1  Nov. 29, 2012

(30) Foreign Application Priority Data
May 23, 2011  (FR) ...................... 11 54452

(51) Int. Cl.
*A01N 1/02* (2006.01)
*A01N 1/00* (2006.01)
*A61B 10/00* (2006.01)
*A47J 41/02* (2006.01)
*F17C 3/08* (2006.01)
*F17C 13/00* (2006.01)
*F25D 3/10* (2006.01)
(Continued)

(52) U.S. Cl.
CPC ........... *A61B 10/0096* (2013.01); *A47J 41/024* (2013.01); *F17C 3/085* (2013.01); *F17C 13/001* (2013.01); *F25D 3/107* (2013.01); *A01N 1/0257* (2013.01); *A61B 17/43* (2013.01); *G01N 2001/005* (2013.01)
USPC ........ 435/284.1; 435/1.1; 435/1.2; 435/289.1

(58) Field of Classification Search
CPC ......... A01N 1/0242; A01N 1/00; A01N 1/02; A01N 1/0236; C12M 21/06; C12M 21/08
USPC ............................. 435/289.1, 1.1, 1.2, 284.1
See application file for complete search history.

(56) References Cited

U.S. PATENT DOCUMENTS

| 2,900,800 A | 8/1959 | Loveday |
| 3,108,840 A | 10/1963 | Conrad et al. |
| 4,154,364 A | 5/1979 | Hagiwara et al. |

(Continued)

FOREIGN PATENT DOCUMENTS

| EP | 0 026 691 A1 | 4/1981 |
| FR | 2 845 973 A1 | 4/2004 |

(Continued)

OTHER PUBLICATIONS

PCT International Search Report and Written Opinion dated Jul. 27, 2012 issued in corresponding PCT Application No. PCT/US2012/039123 (13 pages).

(Continued)

*Primary Examiner* — Nathan Bowers
(74) *Attorney, Agent, or Firm* — Cindee R. Ewell; Ryan Christensen (57) ABSTRACT The invention relates to a portable personal cryogenic container for carrying materials at low temperatures, and more particularly for carrying cryogenically preserved materials. The cryogenic container can be formed from an external shell assembly having multiple parts, where the parts are interlocked to support an inner container. An elongate receptacle holding preserved materials may be supported in the inner container alongside cryogenic fluids for maintaining cryopreserved materials.

32 Claims, 3 Drawing Sheets (51) Int. Cl.
*A61B 17/43* (2006.01)
*G01N 1/00* (2006.01)

(56) References Cited

U.S. PATENT DOCUMENTS

| | | | |
|---|---|---|---|
| 4,266,407 A | | 5/1981 | Gibson |
| 4,512,471 A | | 4/1985 | Kaster et al. |
| 5,355,684 A | * | 10/1994 | Guice ............................. 62/54.2 |
| 5,419,143 A | | 5/1995 | Leonard et al. |
| 5,505,354 A | | 4/1996 | Hutton et al. |
| 5,924,302 A | * | 7/1999 | Derifield ...................... 62/457.2 |
| 6,119,465 A | | 9/2000 | Mullens et al. |
| 6,325,281 B1 | * | 12/2001 | Grogan .................... 229/103.11 |
| 7,581,407 B1 | | 9/2009 | Romanos et al. |
| 2002/0084277 A1 | | 7/2002 | Mullens et al. |
| 2010/0299278 A1 | | 11/2010 | Kriss et al. |
| 2011/0056902 A1 | | 3/2011 | Cognard |

FOREIGN PATENT DOCUMENTS

| | | |
|---|---|---|
| FR | 2868402 A1 | 10/2007 |
| WO | 02/053967 A1 | 7/2002 |
| WO | 02/090821 A2 | 11/2002 |
| WO | 2006055577 A2 | 5/2006 |
| WO | 2008125434 A1 | 10/2008 |

OTHER PUBLICATIONS

French Preliminary Search Report dated Jan. 10, 2012 issued in corresponding FR Application No. 1154452 (14 pages).
France Notice of Grant of Patent dated Jun. 28, 2013, in corresponding FR patent application No. 11 54452.
Canadian Examiner's Requisition issued on Oct. 28, 2014 for Corresponding CA Patent Application No. 2836298.

* cited by examiner

PORTABLE CRYOGENIC CONTAINER

FIELD

The present invention relates to a portable container, and more particularly, to a portable personal container for maintaining cooled or cryopreserved materials.

BACKGROUND

Some materials, such as cells, tissue or other biological materials, require very low temperatures and these materials are often cryogenically preserved with liquid nitrogen at about −196 degrees Celsius for storage and transportation. Maintaining such low temperatures with liquid nitrogen is often handled in one of two ways.

One method including liquid nitrogen cooled materials involves the use of a hermetically sealed container. Since cryogenic fluids, such as liquid nitrogen, transition from a liquid phase to a gas phase during transport, a hermetically sealed container requires a system to control the initial pressure of the interior of the container. Otherwise, pressure builds as the liquid nitrogen expands during this transition. For this reason, hermetically sealed containers can be expensive and bulky, and the required system for controlling the initial pressure can also result in increased costs. Such hermetically sealed containers can only be constructed from bulky materials such as metal, which contributes to an overall weight too great for use as a personal portable container. Due to the brittle nature of glass, it may not be suitable for such hermetically sealed containers because glass may explode as pressure builds within the container.

A second method for transporting liquid nitrogen cooled materials involves the use of a non-hermetically sealed container. Such containers allow nitrogen vapors to escape. These containers should remain upright in order to avoid leakage or spilling of the liquid nitrogen. Often non-hermetically sealed, large metal containers, or cryostats, are used for the transport cryopreserved materials. These containers typically comprise double walled metal containers that have a first wall separated from a second inner wall which holds the liquid nitrogen. The cryostats weight alone contributes significantly to the cost of shipping. Additionally, the long cylindrical shapes of typical cryostats can often put them at risk for tipping during shipment. Such canisters also require complicated valves and lids with pressure release mechanisms, which can significantly increase the cost of producing a non-hermetically sealed container. This can be particularly problematic for cryogenic containers which are only intended for a single use, or for a very limited number of uses.

Regardless of whether the container is hermetically sealed or not, most previous containers for cryopreserved materials were constructed from bulky and heavy metals and lacked the portability. Such containers could require dollies or other mechanical advantages for transport.

Some dry shippers may be lighter containers that include liquid nitrogen absorbing material for the shipment of cryopreserved materials. The liquid nitrogen absorbing material may retain liquid nitrogen for cooling, while reducing or eliminating free flowing liquid nitrogen within the container. Such containers may accommodate suspending a first vessel within a container and may fail to provide a compact and secure cryocontainer suitable for an individual to carry.

DISCLOSURE OF INVENTION

In view of the deficiencies that exist in prior devices, a need exists for a portable cryocontainer. Accordingly, one broad object of certain embodiments of the invention is to provide a compact and light portable personal cryocontainer suitable for an individual to carry cryopreserved materials maintained in a cryopreserved state. Naturally, further objects are disclosed throughout other areas of the specification.

In one embodiment, the invention provides a cryogenic container that includes an external shell assembly having an interior surface defining an interior cavity and an opening to the interior cavity. The external shell assembly may be formed from a first body and a second body. The first body may have a top, a bottom, a first mating surface and a first exterior side opposite the first mating surface. A portion of the first mating surface may be cut away to define a portion of the interior surface of the external shell assembly. Similarly, the second body may have a top, a bottom, a second mating surface and a second exterior side opposite the second mating surface. A portion of the second mating surface may be cut away to define a portion of the interior surface of the external shell assembly. The first mating surface and the second mating surface may be complimentary for interlocking the first body with the second body to form the external shell assembly. An inner container for receiving cryogenic fluid may be supported within the interior cavity of the external shell assembly. And, an elongate receptacle may be placed partially, or completely, within the internal chamber such that elongate receptacle remains accessible from the opening of the external shell assembly.

In another embodiment, a lid may be coupled with the opening of the external shell assembly.

In yet another embodiment, an elongate receptacle may be placed partially, or completely, within the internal chamber such that the elongate receptacle remains accessible from the opening of the external shell assembly. The elongate receptacle may include a closed distal end extending into the internal chamber of the inner container and an open proximal end at the opening of the inner container. A flange and neck may be located at the open proximal end of the elongate receptacle and a perforated region may be located at the closed distal end.

In still another embodiment a permeable sleeve may surround at least a portion of the elongate receptacle and a retrieving arm may be located, at least partially, within the elongate receptacle. The retrieving arm may include a handle accessible from the open proximal end of the elongate receptacle, an offset arm with a first end connected to the handle and a second end, a vertical arm with a terminus connected to the second end of the offset arm, and a catch formed at the terminus of the vertical arm. A canister may be located within the elongate receptacle between the catch formed on the vertical arm and the offset arm of the retrieving arm and insulating filling may be placed within the internal chamber of the inner container for absorbing a cryogenic fluid.

In one embodiment, an insulating filler, such as an absorbent material may be placed in the inner container. The insulating filler may be a calcium silicate or an areogel.

In another embodiment, the container may be configured for maintaining cryopreserved materials for up to 4 days, 5 days, 6 days, or even up to 7 days.

BRIEF DESCRIPTION OF THE DRAWINGS

The foregoing features and other aspects of the invention are explained in the following description taken in conjunction with the following figures.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

Figure 1:
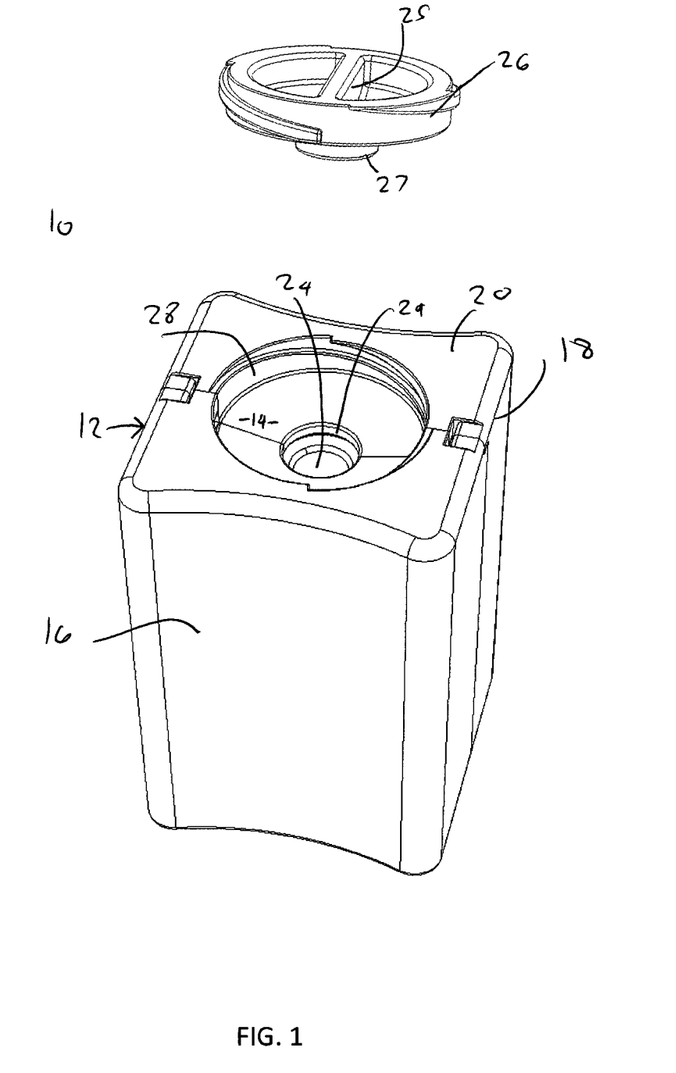
FIG. 1 illustrates an isometric view of a cryogenic container.

Now referring primarily to FIG. 1, a view of a cryogenic container 10 is illustrated. The cryogenic container 10 may be a characterized as a container for transporting materials at low temperatures, such as frozen materials. The cryogenic container 10 may be in the form of a personal container suitable for carrying by an individual. The outermost portion of the cryogenic container 10 can comprise an external shell assembly 12 having an exterior surface 20. The external shell assembly 12 can be constructed from a light weight material, such as extruded or expanded polystyrene. The external shell assembly 12 can be constructed from other materials such as plastics. In one aspect the external shell assembly 12 can be constructed from a light weight material to facilitate an easily portable light weight container, but the material can also be selected for shock or impact absorbing properties. This external shell assembly 12 can include an opening 14 in communication with an interior surface 22 which forms an interior cavity 24. The external shell assembly 12 can be formed from a first body 16 and a second body 18 that are mated or interlocked. The external shell 12 may also be formed from three, four or more bodies. When the first body 16 and the second body 18 are interlocked they can cooperate to form the opening 14. A lid 26 can be configured for coupling to the opening 14 of the external shell assembly 12 for generally closing access to the interior cavity 24. The lid 26 can be constructed from a similar light weight material and can be configured to permit egress of vapors from the interior cavity 24 to the exterior of the external shell assembly 12 thereby preventing pressure from building within the external shell assembly 12 and reducing or eliminating the need for additional pressure releasing systems or elements. This egress of vapors can be achieved by constructing both the external shell assembly 12 and the lid 26 from extruded polystyrene or expanded polystyrene foam. Naturally, other materials may also be used which permit the egress of, for example, liquid nitrogen vapors from the interior of the inner container 30 (seen in FIG. 2). The lid 26 can be coordinated with the opening 14 to maximize the insulation provided. However, plastics may also be used to construct the external shell assembly 12.

The opening 14 can comprise a first bored region 28 in the external shell assembly 12 at the top surfaces of the first body 16 and the second body 18. The first bored region 28 can be threaded for receiving threads on the lid 26. The opening 14 can further comprise a second bored region 29 of a smaller diameter than the first bored region 28 which extends to the interior cavity 24, thereby permitting access to the interior cavity 24 from the exterior of the container 10 when the lid 26 is removed. An extension 27 on the lid 26 can be dimensioned for coupling with this diameter of the second bored region 29. The lid 26 can further comprise a grip 25 useable to effect the threading and unthreading of the lid 26 with the opening 14.

Figure 2:
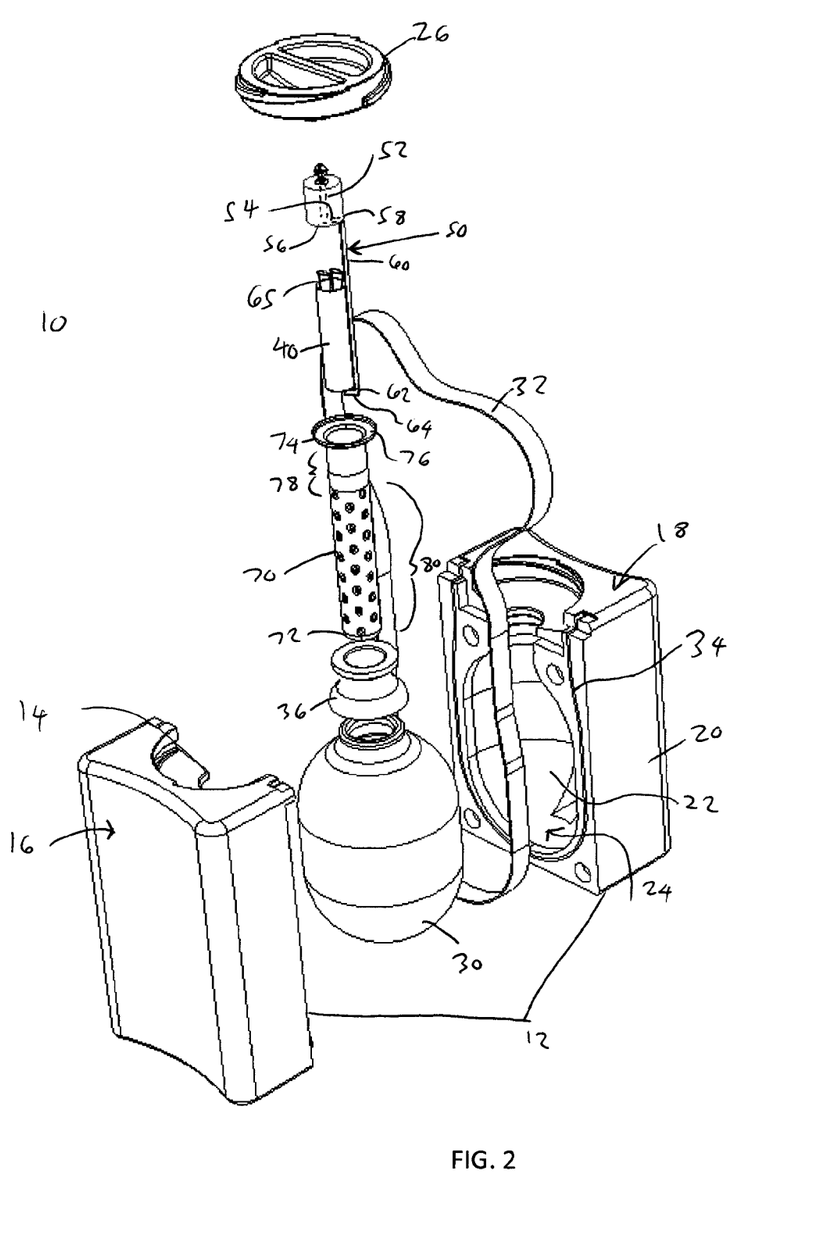
FIG. 2 illustrates an exploded view of a cryogenic container.

Referring primarily to FIG. 2, an exploded view of the cryogenic container 10 is illustrated. The interior surface 22 of the interior cavity 24 is visible on the inside section of the second body 18 and can be formed for supporting an inner container 30. The inner container 30 can be a Dewar vessel comprising an inner wall and connected to an outer wall at an opening of the inner container 30 forming an internal chamber. The inner and outer walls can be separated by a space which can be a vacuum. This vacuum minimizes heat transfer via convection or conduction from the interior chamber to the exterior of the inner container 30. The inner container 30 can be constructed as glass lined with a reflective coating on the exterior of the outer wall and on the interior of the inner wall to reduce to reduce heat transferred by radiation. Other suitable inner containers may also be used, such as alternative vacuum vessels, thermos containers, or other insulated containers. The inner container 30 can comprises an internal chamber defined by the inner wall capable of receiving the cryogenic fluid, such as liquid nitrogen. A neck 36 can be formed integrally with the inner container 30 at an opening or can be attached thereto.

An elongate receptacle 70 having a closed distal end 72 and an open proximal end 74 can be stored, at least partially, within the interior chamber of the inner container 30. The inner container 30 can also be filled with an absorbent material, such as foam, calcium silicate, or an aerogel. Calcium silicate and aerogel can serve to absorb liquid nitrogen thereby forming a dry shipping container. Calcium silicate and aroegels are some examples of absorbents that may be used, but other absorbents are contemplated for use herein, including other hydrophobic and non-hydrophobic absorbent materials. Generally, the elongate receptacle 70 can be suspended from the inner container 30 occupying a central portion of the inner container 30, while the absorbing material can occupy the remaining space around the elongate member 70 within the inner container 30. The proximity of the absorbent filling to the elongate receptacle provides the required refrigeration, when charged with a cryogenic material.

The elongate receptacle 70 can have a flange 76 at the open proximal end 74 which can rest on the neck 36 thereby providing a stopping point for the elongate receptacle 70 within the inner container 30. When the external shell assembly 12 is intact, the flange 76 is provided such that the open proximal end 74 is primarily the only space accessible from the opening 14. More particularly, the open proximal end 74 can be the only space accessible from the second bored region 29 of the opening 14. In this way, the flange 76 helps to isolate the inner container 30 at its neck 36, where significant heat transfer may occur. The elongate receptacle 70 can comprise a first region along its length, such as a neck region 78 at the open proximal end 74. The elongate receptacle 70 can further comprise a perforated region 80 towards the distal closed end 72. The perforated region 80 can include openings spaced and dimensioned to allow a cryogenic fluid to flow through the elongate receptacle 70 into the remaining area of the inner container 30 when poured into the open proximal end 74. The cryogenic fluid can then be distributed and absorbed by the absorbent located outside the elongate receptacle 70. The elongate receptacle 70 can be covered with a permeable sleeve which allows liquids to pass easily, but which prevents the absorbent material from entering the elongate receptacle 70.

Biological samples 65 are illustrated within a canister 40 that can be stored in the elongate receptacle 70. The canister 40 can be a goblet for holding a plurality of biological samples 65. As but one example, the biological samples 65 can comprise individual 0.25 ml straws of frozen semen. Other biological samples, such as frozen embryos, other frozen tissues or other frozen cells may also be transported within the canister 40. Generally, the canister 40 can retrievably rest at the closed distal end 72 of the elongate receptacle 70. A retrieving arm 50 can also rest in the elongate receptacle 70. The retrieving arm 50 can have a first end accessible from the open proximal end 74 of the elongate receptacle in addition to a second end which rests at the closed distal end 72. At the first end the retrieving arm 50 can have a handle 52, which can be attached to an offset arm 54. The handle 52 can comprise a gripping portion for withdrawing the retrieving arm 50 from the elongate receptacle 80, as well as insulation or padding for substantially filling the interior space in the neck 78 of the elongate receptacle 70 in order to reduce the loss of refrigeration in the inner container 30 through the opening 14.

The handle 52 can be connected to a first end 56 of an offset arm 54, which can run generally perpendicular to the handle 52. The second end 58 of the offset arm 54 can connect to a vertical arm 60. Whereas the handle 52 can be disposed within the elongate receptacle 70 at a generally central coaxially location, the vertical arm 60 can be offset by the offset arm 54 for generally running along the side of the interior of the elongate receptacle 70. At the terminus 62 of the vertical arm 60 a catch 64 can be formed. The catch 64 can be configured such that the canister 40 generally rests on the catch 64 within the elongate receptacle 70. In this arrangement, actuating the retrieving arm 50 from the elongate receptacle 70 can be used to retrieve the canister 40 from the closed distal end 72 of the elongate receptacle 70.

A slot 34 can be seen in the second body 18 for receiving a strap 32. This strap 32 in combination with the contour of each of the first body 16 and the second body 18 provides an ergonomic means for carrying this light weight cryogenic container.

Figure 3A:
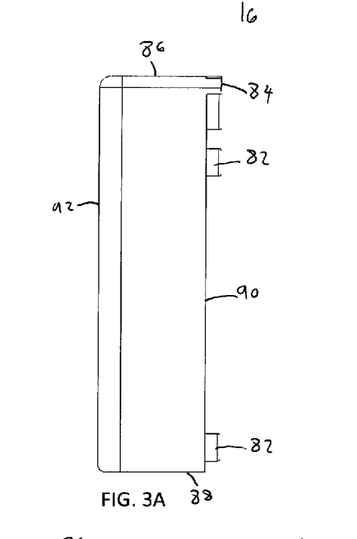
FIG. 3A illustrates a side view of a first body for forming an external shell assembly.
Figure 3B:
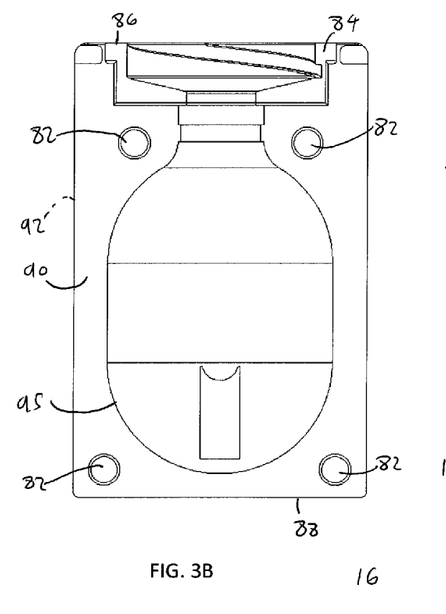
FIG. 3B illustrates a front view of a first body for forming an external shell assembly.

Referring primarily to FIGS. 3A and 3B a front view and a side view depicts the interlocking features of the first body 16. The first body 16 is illustrated with a top 86, a bottom 88, a first mating surface 90 and a first exterior side 92. The first mating surface 90 can be seen with a first cut away portion 95 which corresponds to the inner container 30. With reference to FIGS. 1 and 2, the first exterior side can be seen as a curved surface. Additionally, the mating surface of the first body 16 can include a plurality of alignment protrusions 82, in addition to an alignment lip 84.

As can be better seen with reference to FIG. 2, the first exterior side 92 can be contoured for comfort. Namely, the surface of the first exterior side 92 can be curved for resting comfortably against the side torso or hip of an individual carrying the cryogenic container 10 with the strap 32 over the shoulder. The shape employed by the surface may be referred to as an ergonomically curved surface and may additionally provide the benefit of improved stability while being carried.

Figure 4A:
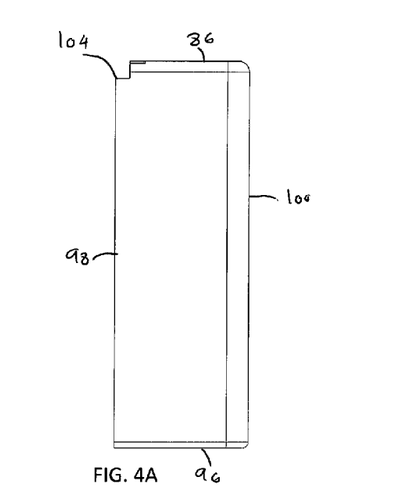
FIG. 4A illustrates a side view of a second body for forming an external shell assembly.
Figure 4B:
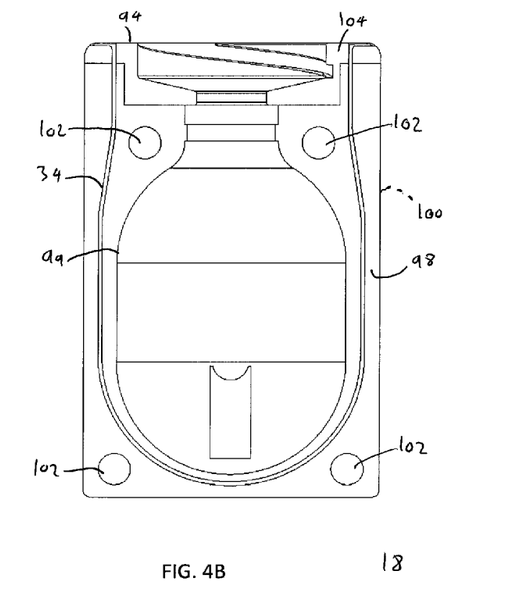
FIG. 4B illustrates a front view of a second body for forming an external shell assembly.

Now referring primarily to FIGS. 4A and 4B a front view and a side view is illustrated depicting the interlocking features of the second body 18. The second body 18 is illustrated with a top 94, a bottom 96, a second mating surface 98, and a second exterior side 100. The second mating surface 98 can be seen with a second cutaway portion 99 for supporting the inner container 30 when mated with the first body 16. The second mating surface 98 can further comprise a plurality of receiving openings 102 for receiving the alignment protrusions 82 of the first body 16. These alignment protrusions 82 and receiving openings 102 can be aligned such that each of the remaining sides of the first body 16 and the second body 18 are generally flush. The second mating surface can further include an alignment notch 104 for receiving the alignment protrusion 84. Referring back to FIG. 2, the second exterior side 100 can be contoured for comfort, in lieu of, or in addition to the first exterior side having an ergonomically curved surface.

A slot 34 for receiving the strap 32 can be seen carved into the second body, although it should be appreciated, such a slot could be carved in the first body, or affixed to the exterior surface 20 of the cryogenic container 10. The second exterior side 100 can also be contoured to promote comfort and ease in handling.

As can be easily understood from the foregoing, the basic concepts of the present invention may be embodied in a variety of ways. The invention involves numerous and varied embodiments of cryogenic containers. As such, the particular embodiments, elements, terms, or expressions disclosed by the description, or shown in the figures, accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "container" should be understood to encompass disclosure of the act of "containing"—whether explicitly discussed or not—and, conversely, were there effectively disclosure of the act of "containing", such a disclosure should be understood to encompass disclosure of a "container" and even a "means for containing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a container" refers to one or more of the containers. As such, the terms "a" or "an", "one or more" and "at least one" can be used interchangeably herein.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A cryogenic container comprising:
   a. an external shell assembly having an interior surface defining an interior cavity, the interior surface being in communication with an exterior surface through an opening, the external shell assembly further comprising:
      i. a first body having a top, a bottom, a first mating surface and a first exterior side opposite the first mating surface, a portion of the first mating surface being cut away to define a portion of the interior surface of the external shell assembly;
      ii. a second body having a top, a bottom, a second mating surface and a second exterior side opposite the second mating surface, a portion of the second mating surface being cut away to define a portion of the interior surface of the external shell assembly, wherein the first mating surface and the second mating surface are complimentary for interlocking the first body with the second body;
      iii. a threaded first bored region and a second bored region forming the opening in the external shell assembly, the second bored region proving access to the interior of the external shell assembly;
   b. an inner container, having an internal chamber for receiving cryogenic fluid, supported within the interior cavity of the external shell assembly by the interior surface of the external shell assembly;
   c. an elongate receptacle located at least partially within the internal chamber of the inner container accessible from the opening of the external shell assembly; and
   d. a threaded lid for coupling to the threaded first bored region of the external shell assembly, the threaded lid being configured to permit the egress of vapor when coupled to the first bored region of the external shell assembly, and wherein the lid comprises an extension at the bottom, the extension being dimensioned for coupling with the second bored region.

2. The cryogenic container of claim 1 wherein the inner container comprises a Dewar vessel.

3. The cryogenic container of claim 2 wherein the Dewar vessel comprises an inner wall connected to an outer wall at an opening of the inner container, and wherein the inner wall and the outer wall are separated by a vacuum.

4. The cryogenic container of claim 3 wherein the Dewar vessel is constructed from glass.

5. The cryogenic container of claim 1 wherein the cryogenic fluid comprises liquid nitrogen.

6. The cryogenic container of claim 1 further comprising a canister within the elongate receptacle for holding materials.

7. The cryogenic container of claim 6 further comprising a retrieving arm for retrieving the canister from the elongate receptacle.

8. The cryogenic container of claim 7 wherein the retrieving arm further comprises:
   a. a handle accessible from the opening;
   b. an offset arm with a first end and a second end, the offset arm being connected to the handle at the first end;
   c. a vertical arm with a terminus connected to the second end of the offset arm; and
   d. a catch formed at the terminus of the vertical arm.

9. The cryogenic container of claim 8 wherein the handle further comprises a gripping portion and a padded portion, wherein the padded portion is dimensioned to match the interior of the elongate receptacle.

10. The cryogenic container of claim 1 wherein the interior chamber of the inner container includes an insulating filling.

11. The cryogenic container of claim 10 wherein the insulating filling comprises calcium silicate or aerogel.

12. The cryogenic container of claim 10 wherein, when charged with a cryogenic fluid, the insulating filling provides a period of storage selected from the following: up to 4 days, up to 5 days, up to 6 days, and up to 7 days.

13. The cryogenic container of claim 1 wherein the elongate receptacle has a closed distal end extending into the internal chamber of the inner container and an open proximal end at the opening of the inner container, the elongate receptacle further comprising:
   i. a flange at the open proximal end;
   ii. a neck region formed at the open proximal end; and
   iii. a perforated region at the closed distal end.

14. The cryogenic container of claim 1 wherein the first body and the second body of the external shell assembly comprise two complementary pieces such that when the first mating surface is interlocked with the second mating surface mated the external shell assembly is formed with an interior surface defining an interior cavity connected to an exterior surface through the opening.

15. The cryogenic container of claim 14 wherein the first body further comprises at least one alignment protrusion.

16. The cryogenic container of claim 15 wherein the second body further comprises at least one receiving opening for receiving the at least one alignment protrusion when the first body is interlocked with the second body.

17. The cryogenic container of claim 15 wherein the second body further comprises an alignment notch.

18. The cryogenic container of claim 17 wherein the second body further comprises at least one alignment lip configured for mating with the alignment notch when the first body is interlocked with the second body.

19. The cryogenic container of claim 1 further comprising a permeable sleeve around at least a portion of the elongate receptacle.

20. The cryogenic container of claim 1 wherein the opening further comprises a first bored region at one size and a second bored region at a reduced size compared to the first bored region.

21. The cryogenic container of claim 20 wherein the side of the lid matches the first bored region and the extension matches the second bored region.

22. The cryogenic container of claim 1 further comprising a strap.

23. The cryogenic container of claim 22 wherein the external shell assembly further comprises a slot for receiving the strap.

24. The cryogenic container of claim 1 wherein the materials transported at low temperatures comprise cryogenically preserved biological materials.

25. The cryogenic container of claim 24 wherein the cryogenically preserved biological materials comprise reproductive cells.

26. The cryogenic container of claim 24 wherein the reproductive cells are selected from the group consisting of: eggs, oocytes, sperm, semen, sex-selected sperm, embryos sex selected embryos and combinations thereof.

27. The cryogenic container of claim 1 wherein the cryogenic container comprises a personal container for carrying by an individual.

28. The cryogenic container of claim 1 wherein the loaded weight of the container is selected from the list consisting of: less than 10 kg, less than 5 kg, and less than 4 kg.

29. The cryogenic container of claim 1 wherein at least one of the first exterior side and/or the second exterior side comprise an ergonomically curved surface for resting against the side of an individual during transport.

30. The cryogenic container of claim 1 wherein the external shell assembly further comprises a third body.

31. The cryogenic container of claim 30 wherein the external shell assembly further comprises a fourth body.

32. A personal container for transporting materials at low temperatures comprising:
  a. an external shell assembly having an interior surface defining an interior cavity, the interior surface being in communication with an exterior surface through an opening, the external shell assembly further comprising:
    i. a first body having a top, a bottom, a first mating surface and a first exterior side opposite the first mating surface, a portion of the first mating surface being cut away to define a portion of the interior surface of the external shell assembly;
    ii. a second body having a top, a bottom, a second mating surface and a second exterior side opposite the second mating surface, a portion of the second mating surface being cut away to define a portion of the interior surface of the external shell assembly, wherein the first mating surface and the second mating surface are complimentary for interlocking the first body with the second body;
    iii. a threaded first bored region and a second bored region forming the opening in the external shell assembly, the second bored region proving access to the interior of the external shell assembly;
  b. a threaded lid for coupling to the threaded first bored region of the external shell assembly, the threaded lid being configured to permit the egress of vapor when coupled to the first bored region of the external shell assembly, and wherein the lid comprises an extension at the bottom, the extension being dimensioned for coupling with the second bored region;
  c. an inner container having an opening in communication with an internal chamber, wherein the inner container is supported within the interior cavity of the external shell assembly by the interior surface of the external shell assembly when the first body and the second body are interlocked around the inner container, the inner container further comprising:
    i. an inner wall with a reflective coating on an interior surface;
    ii. an outer wall with a reflective coating on an exterior surface; and
    iii. a vacuum separating the inner wall from the outer wall, wherein the inner wall and the outer wall are joined at the opening of the inner container;
  d. an elongate receptacle with a closed distal end extending into the internal chamber of the inner container and an open proximal end at the opening of the inner container, the elongate receptacle further comprising:
    i. a flange at the open proximal end;
    ii. a neck region formed at the open proximal end; and
    iii. a perforated region at the closed distal end;
  e. a permeable sleeve around at least a portion of the elongate receptacle;
  f. a retrieving arm located, at least partially, within the elongate receptacle, the retrieving arm comprising:
    i. a handle accessible from the open proximal end of the elongate receptacle;
    ii. an offset arm with a first end and a second end, the offset arm being connected to the handle at the first end;
    iii. a vertical arm with a terminus connected to the second end of the offset arm; and
    iv. a catch formed at the terminus of the vertical arm;
  g. a canister located within the elongate receptacle between the catch formed on the vertical arm and the offset arm of the retrieving arm; and
  h. an insulating filling within the internal chamber of the inner container for absorbing a cryogenic fluid.

* * * * *

UNITED STATES PATENT AND TRADEMARK OFFICE
CERTIFICATE OF CORRECTION

PATENT NO. : 8,956,855 B2
APPLICATION NO. : 13/478791
DATED : February 17, 2015
INVENTOR(S) : Eric Cognard and Juan Moreno It is certified that error appears in the above-identified patent and that said Letters Patent is hereby corrected as shown below:

In the Claims,

Column 9, claim 26, line 26, "embryos sex" should be replaced with -- embryos, sex --

Signed and Sealed this
Twenty-third Day of June, 2015

Michelle K. Lee
*Director of the United States Patent and Trademark Office*